United States Patent
Squicciarini

[11] Patent Number: 5,647,744
[45] Date of Patent: Jul. 15, 1997

[54] SET OF CASTING ELEMENTS FOR THE REALIZATION OF GYPSUM MODELS FOR DENTAL PROSTHESIS, AND CASTING SYSTEMS EMPLOYING SAID ELEMENTS

[76] Inventor: Gaetano Squicciarini, No. 15, Largo dell'Olgiata, Isola 80L1-00123, Rome, Italy

[21] Appl. No.: 506,694

[22] Filed: Jul. 25, 1995

[30] Foreign Application Priority Data

Jul. 27, 1994 [IT] Italy .................. RM94A0500

[51] Int. Cl.⁶ .................................. A61C 19/00
[52] U.S. Cl. .................. 433/34; 433/74; 433/213
[58] Field of Search ................. 433/74, 60, 34, 433/213

[56] References Cited

U.S. PATENT DOCUMENTS

| | | |
|---|---|---|
| 2,337,036 | 12/1943 | Erdle ........................................... 433/34 |
| 3,161,917 | 12/1964 | Wiland . |
| 3,650,032 | 3/1972 | Kestler ........................................ 433/74 |
| 4,203,219 | 5/1980 | Wiener ........................................ 433/74 |
| 4,283,173 | 8/1981 | Browne et al. ............................. 433/34 |
| 4,300,884 | 11/1981 | Camacho .................................... 433/74 |
| 4,494,934 | 1/1985 | Huffman .................................... 433/213 |
| 4,842,242 | 6/1989 | Huffman ..................................... 433/60 |

FOREIGN PATENT DOCUMENTS

| | | |
|---|---|---|
| 0277027 | 8/1988 | European Pat. Off. . |
| 4028728 | 3/1992 | Germany . |

*Primary Examiner*—Cary E. O'Connor
*Attorney, Agent, or Firm*—Beveridge, DeGrandi, Weilacher & Young, L.L.P.

[57] ABSTRACT

The invention concerns a set of casting elements for the realization of gypsum models for dental prothesis comprising a series of elements made up of rubber material opened above and at the bottom, and perimetrically closed, shaped in such a way to allow the inner coupling from the lower side to corresponding impression carrier. The invention also relate to a casting system employing the elements.

21 Claims, 8 Drawing Sheets

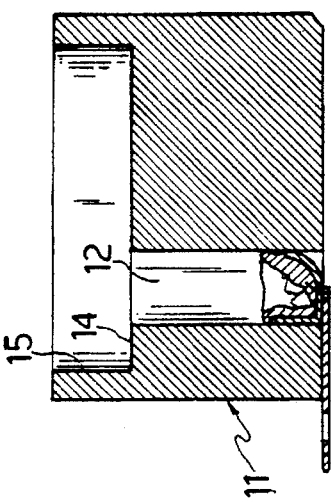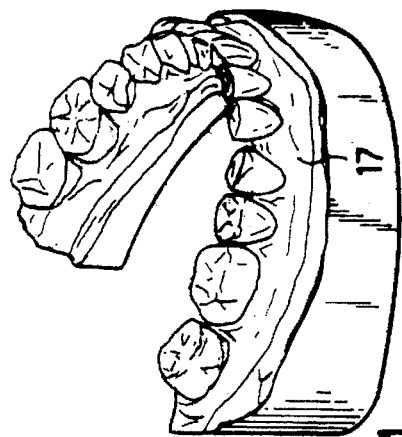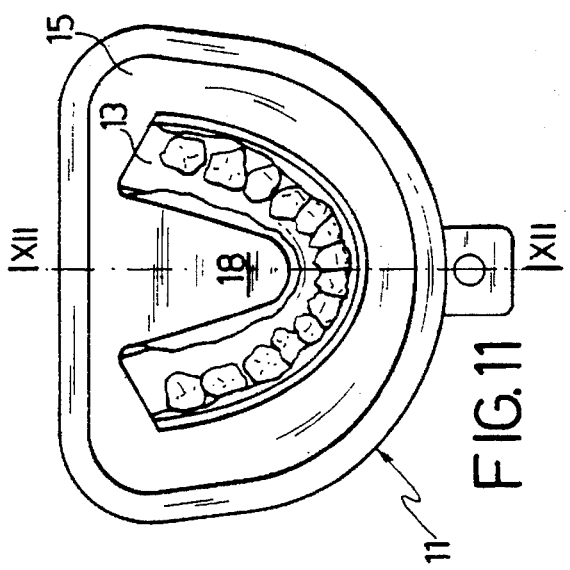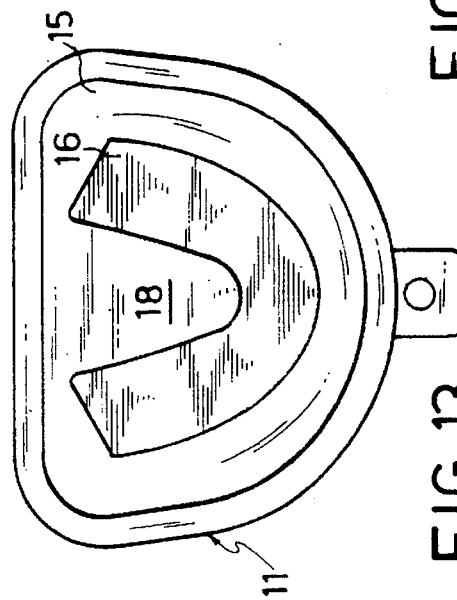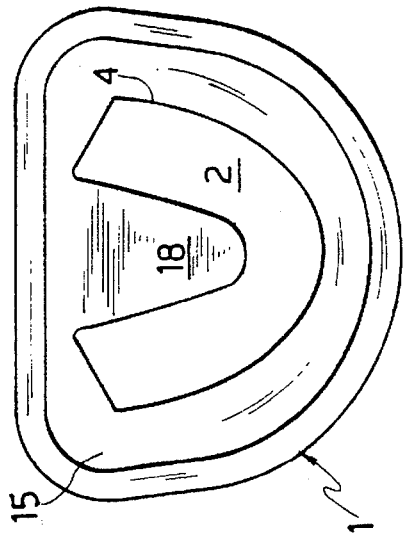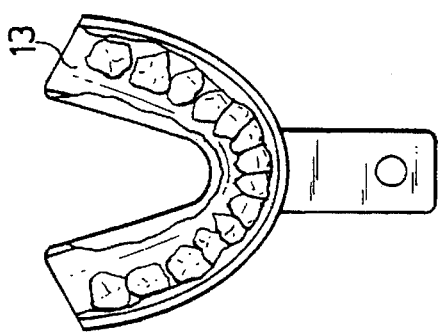

SET OF CASTING ELEMENTS FOR THE REALIZATION OF GYPSUM MODELS FOR DENTAL PROSTHESIS, AND CASTING SYSTEMS EMPLOYING SAID ELEMENTS

The present invention relates to a set of casting elements for the realization of gypsum models for dental prosthesis.

The invention also relates to casting methods employing said elements.

At present, the casting of gypsum for the realization of dental prosthesis models is realized manually, i.e. casting the gypsum directly without any constraint.

This solution brings to the obtainment of a very coarse product, which to be positively realized must be subjected to various operations.

Further, this kind of solution does not allow the model to have a height of specific needing.

As to a kind of working usually named Zeiser, requiring the introduction of pins on a Plexiglas plate, remarkably complicated apparatuses are employed, said apparatuses being difficult to be used and not allowing to obtain an optimum result to be obtained.

In view of the above, the Applicant has realized a set of elements that allows the casting for the realization of gypsum models for the subsequent realization of prosthesis to easily, precisely and rapidly obtain gypsum models.

The solution proposed according to the invention provides the realization of rubber material elements, having different sizes in order to be able to realize every kind of model, so shaped to obtain both palatal and lingual models.

By the solution according to the present invention a modern system is obtained, said system being very simple and fast during the casting of the gypsum impressions, thus offering a great saving of time, of workers, of material and of money.

Further, the solution proposed according to the present invention allows to the dental technician and the dentist the choice of the height of the model.

Still further, the finishing obtained gives the opportunity, as soon as released the impression, by the aid of a known articulator, to immediately begin the work without the positioning in the gypsum articulator. In fact, its squared and smooth shape allows the precise and direct introduction on the articulator In the set according to the invention, each element is marked by an alpha-numeric acronym corresponding to the size of the impression carrier.

It is therefore specific object of the present invention a set of casting elements for the realization of gypsum models for dental prosthesis, comprising a series of elements made up of rubber material, opened above and at the bottom, and perimetrically closed, shaped in such a way to allow the inner coupling from the lower side of the corresponding impression carrier.

Preferably, according to the invention, said elements are made up of silicone material.

Still according to the invention, in the inner part of said elements a step is provided at a height leaving lower down a zone having dimensions corresponding to the dimensions of the model to be realized, the step allowing to avoid a lateral leakage of the cast gypsum.

Further, according to the invention, a second step can be provided for the introduction of a Plexiglas plate for the positioning of the metal pins, making it possible to provide the second step together or independently from the first step.

Still according to the invention, the elements can be provided with a central projection corresponding to the lingual shaping.

It is further object of the invention a casting system employing said elements, comprising the steps of:
taking the impression by an impression carrier and eliminating the exceeding material;
introducing the impression carrier lower down the corresponding element, eventually closing little slits by a suitable material;
casting the gypsum, preferably on a vibrator;
disconnecting the impression from the gypsum carrier.

In case of working according to the Pindex system, the casting system according to the invention comprises the following steps of:
taking the impression by an impression carrier and eliminating the exceeding material;
introducing the impression carrier lower down the corresponding element eventually closing little slits by a suitable material;
introducing the pins on teeth prepared in the silicon impression covering the end of the metal pin by a little soft wax ball;
casting the gypsum, preferably on a vibrator up to the initial part of the metallic sheath of the pin;
after the hardening, isolating the gypsum in correspondence of the pins, and completing the casting of the impression employing gypsum having a different color;
after the casting and the hardening of the gypsum, separating by a hacksaw the teeth provided with the pins.

Still according to the invention, in case of working with the Zeiser system, the casting system provides the following steps of:
taking the impression by an impression carrier and eliminating the exceeding material;
introducing the impression carrier lower down the corresponding element eventually closing little slits by a suitable material;
bringing the element with the impression carrier introduced in the element for piercing the gypsum, introducing the Plexiglas plate and marking the pin positioning points;
releasing and turning over the Plexiglas plate and realizing the holes for the pins;
introducing the pins in their position;
casting an hard gypsum, preferably on a vibrator and thus placing again the Plexiglas plate;
after the hardening, removing the model with the Plexiglas plate and refining the same;
separating the teeth provided with the pins employing a hacksaw.

The present invention will be now described for illustrative, but not limitative purposes, according to its preferred embodiments with particular reference to the enclosed drawings, wherein:

FIG. 9 is a plan view of the element of FIG. 8;

FIG. 10 is a plan view of an impression carrier usable with the element of FIG. 8;

FIG. 11 is a plan view of the element of FIG. 8 and of the impression carrier of FIG. 8 coupled;

FIG. 12 is a section view along the line XII—XII of FIG. 11;

FIG. 13 is a plan view of the components of FIG. 11 after the casting of the gypsum;

FIG. 14 is a perspective view of a model realized by the set according to the invention;

In FIGS. 1 to 14 a first embodiment of the set of casting elements gypsum impressions according to the invention is shown.

It must in any case preliminarily be noted that the various elements are described with reference to a single size, but it is to be understood that the set according to the invention can comprise different elements similar to those described, only having different dimensions.

This kind of observation must be considered valid also for embodiment that will be described with reference to the FIGS. 15–28.

In FIGS., 1 to 7 it is shown an element 1 of the first embodiment, and its utilization for the palatal zone of the mouth.

Figure 3:
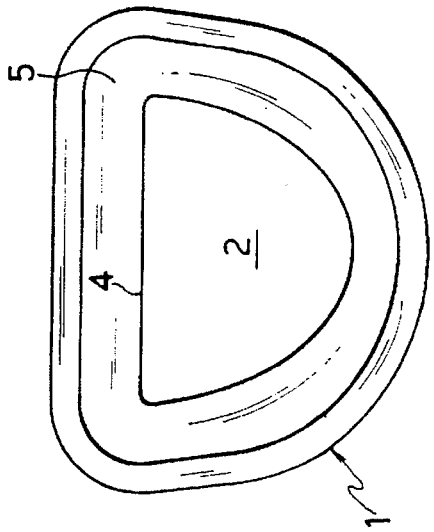
FIG. 3 is a plan view of a carrier impression to be used with the element of FIG. 1.

Said element is made up of silicone material and provides an inner zone 2, coupable with the impression carrier 3 of FIG. 3, by which the impression of the patient has been taken in the usual manner, and a junction step 4 with a upper containment zone 5, to impede the leakage of the cast gypsum.

Figure 1:
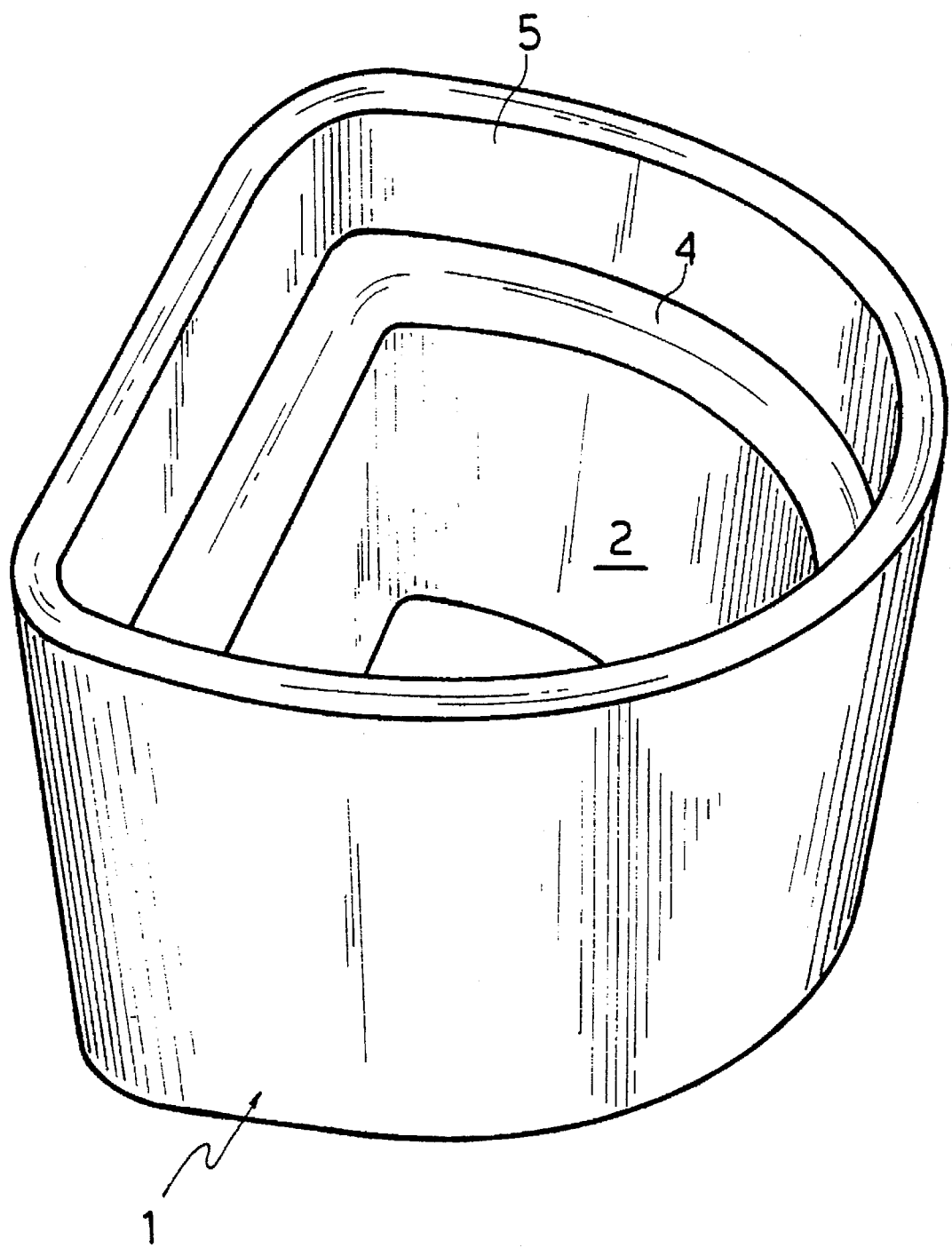
FIG. 1 is a perspective view of a first element of a first embodiment of the set for casting gypsum models according to the inventions.
Figure 2:
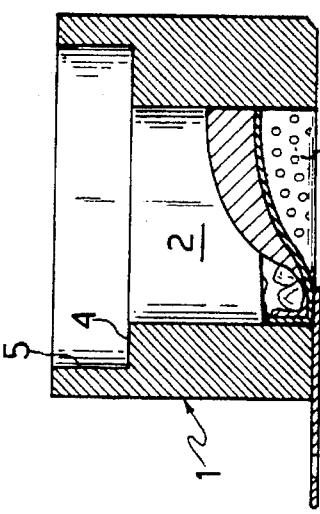
FIG. 2 is a plan view of the element of FIG. 1.
Figure 5:
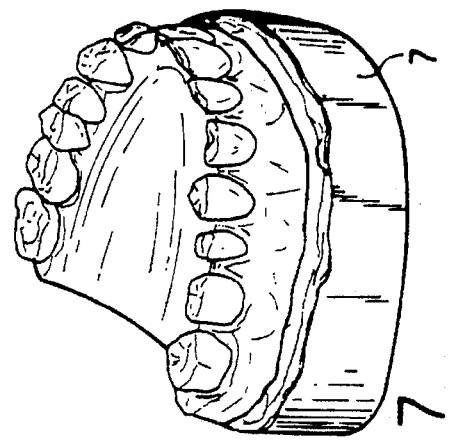
FIG. 5 is a section view along the line V—V of FIG. 4.
Figure 4:
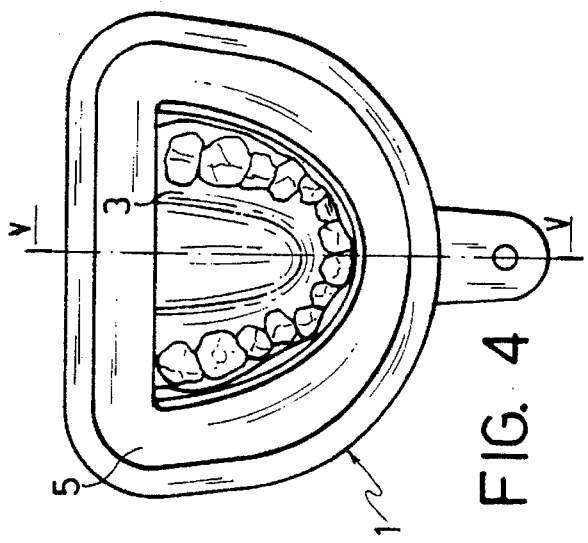
FIG. 4 is a plan view of the element of FIG. 1 and of the impression carrier of FIG. 3 coupled.

The impression carrier 3 and the element 1 are coupled to each other as shown in FIGS. 4 and 5.

Figure 6:
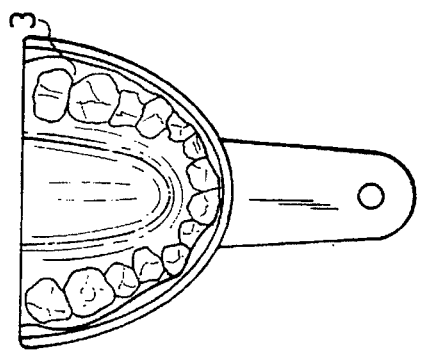
FIG. 6 is a plan view of the components of FIG. 4 after the casting of the gypsum.
Figure 8:
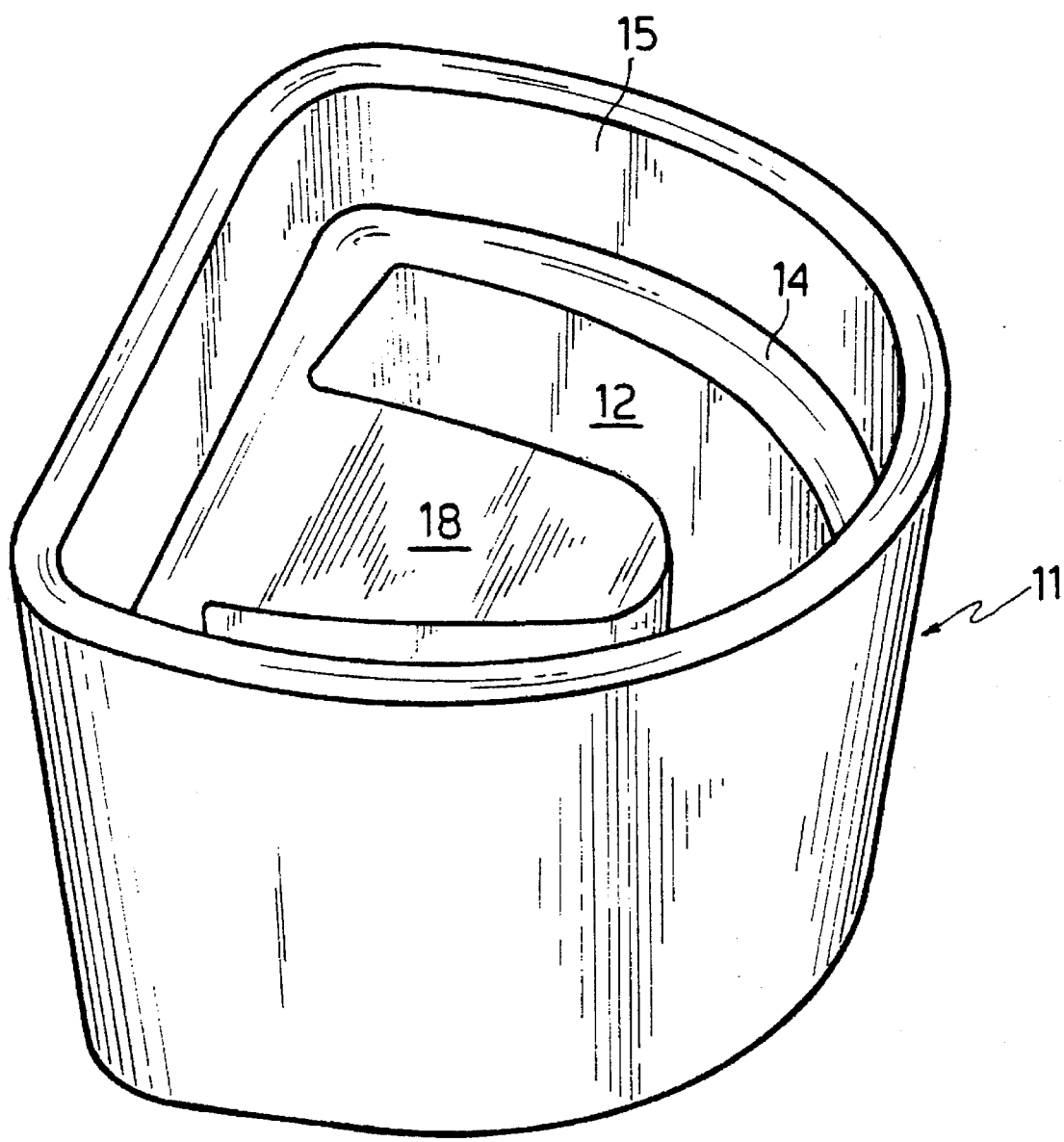
FIG. 8 is a perspective view of a second element of a first embodiment of the set for casting of gypsum models according to the invention.
Figure 15:
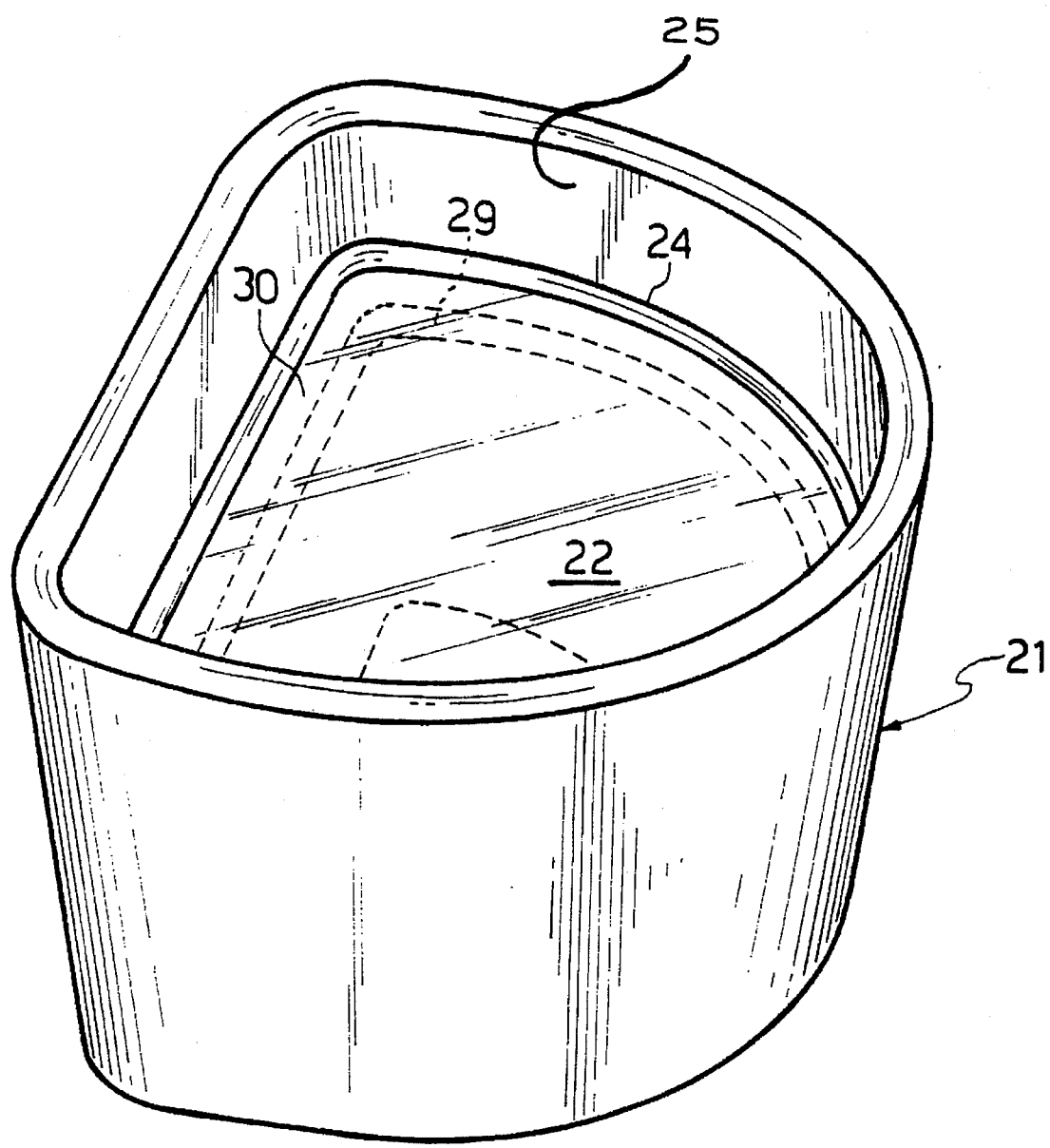
FIG. 15 is a perspective view of a first element of a second embodiment of the set for casting gypsum models according to the inventions.

FIG. 6 shows the element 1 and the impression carrier 3 after the casting of the gypsum 6.

Figure 7:
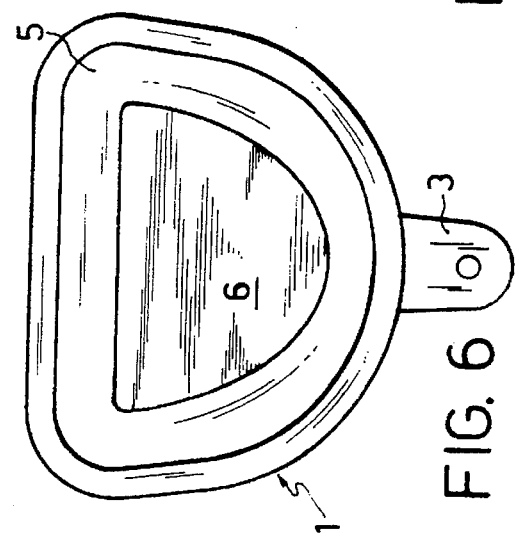
FIG. 7 is a perspective view of a model realized by the set according to the invention.

FIG. 7 shows the final result, with the obtained model 7.

In FIGS. 8 to 14, an element 11 is shown, as well as the relevant use for the lingual zone of the mouth.

Substantially, the functionality of the element 11 and its realization are the same as the element 1 previously described, so that the same elements and features are indicated by the same numeral reference, preceded by the number 1.

The difference that can be noted is the one relevant to the shaped projection 18 corresponding to the shape of the impression carrier 13 shown in FIG. 10.

A first kind of utilization of the set described with reference to FIGS. 1–14 can be described as follow.

First, the exceeding impression material (alginate or silicon) coming out from the impression carrier 3 (13) is eliminated by a lancet or by a cutter so as to obtain a perfect insertion and adhesion between the impression and the element 1 (11) walls.

Thus, the numbered or marked (according to the manufacturer) impression carrier 3 (13) is inserted in its element 1 (11). In case a little sit occurs between the impression carrier 3 (13) and the element 1 (11), it can be closed by some plasticine so that the gypsum does not come out.

It is advisable to cast the impression on a vibrator.

As soon as the cast gypsum 6 (16) (see FIGS. 6 and 13) hardened, the impression carrier is disconnected from the element 1 (11).

It can be immediately noted the exact refining and smoothing of the model 7 (17) that is obtained (see FIGS. 7 and 14).

The lower model does not need the removal of gypsum in the lingual zone, but as it can be noted, an already refined lingual zone is obtained.

It will be easy to note for one skilled in the art the enormous difference between the traditional casting of models without the set according to the invention and the new casting suggested according to the invention.

In case the sharp corner should be eliminated from the gypsum impression in order to obtain a more refined model in the fornux zones and in the lingual zones, it is sufficient to employ a gypsum mill.

The models released are introduced within the articulators, e.g. J. Morita (Japanese) or Galletti, etc., thus obtaining a perfect refining of the models and a perfect restrained joint with the basis of the same articulators.

The set shown in FIGS. 1–14 can be also used for the working of the so called Pindex system.

In this case too, first the exceeding impression material (alginate or silicon) coming out from the impression carrier 3 (13) is eliminated by a lancet or a cutter so as to obtain a perfect insertion and adhesion between the impression and the element 1 (11) walls.

Then the pins (not shown) are inserted on the teeth prepared in the silicon impression covering the end of the metal pin with a little soft wax ball.

After this step, a hard gypsum is cast so as to cover the prepared stumps up to the initial part of the metallic sheath.

When the gypsum hardens, the gypsum is insulated in correspondence of the pins, and the impression cast is terminated preferably with a differently colored gypsum up to the step.

In this way the exact height for the working of the Pindex system with a refined gypsum base is obtained.

Finally, the Gypsum model is brought on the hacksaw for stumps and the teeth with the inserted pins are separated.

Also in this case the workability on the articulators is optimal.

In FIGS. 15 to 28 it is shown a second embodiment of the set according to the invention.

In FIGS. 15 to 21, an element 21, and the relevant utilization, is shown for the palatal zone of the mouth.

Figure 17:
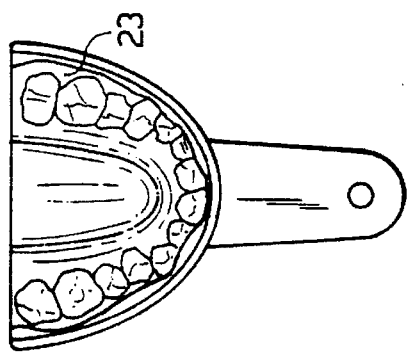
FIG. 17 is a plan view of a carrier impression to be used with the element of FIG. 15.
Figure 22:
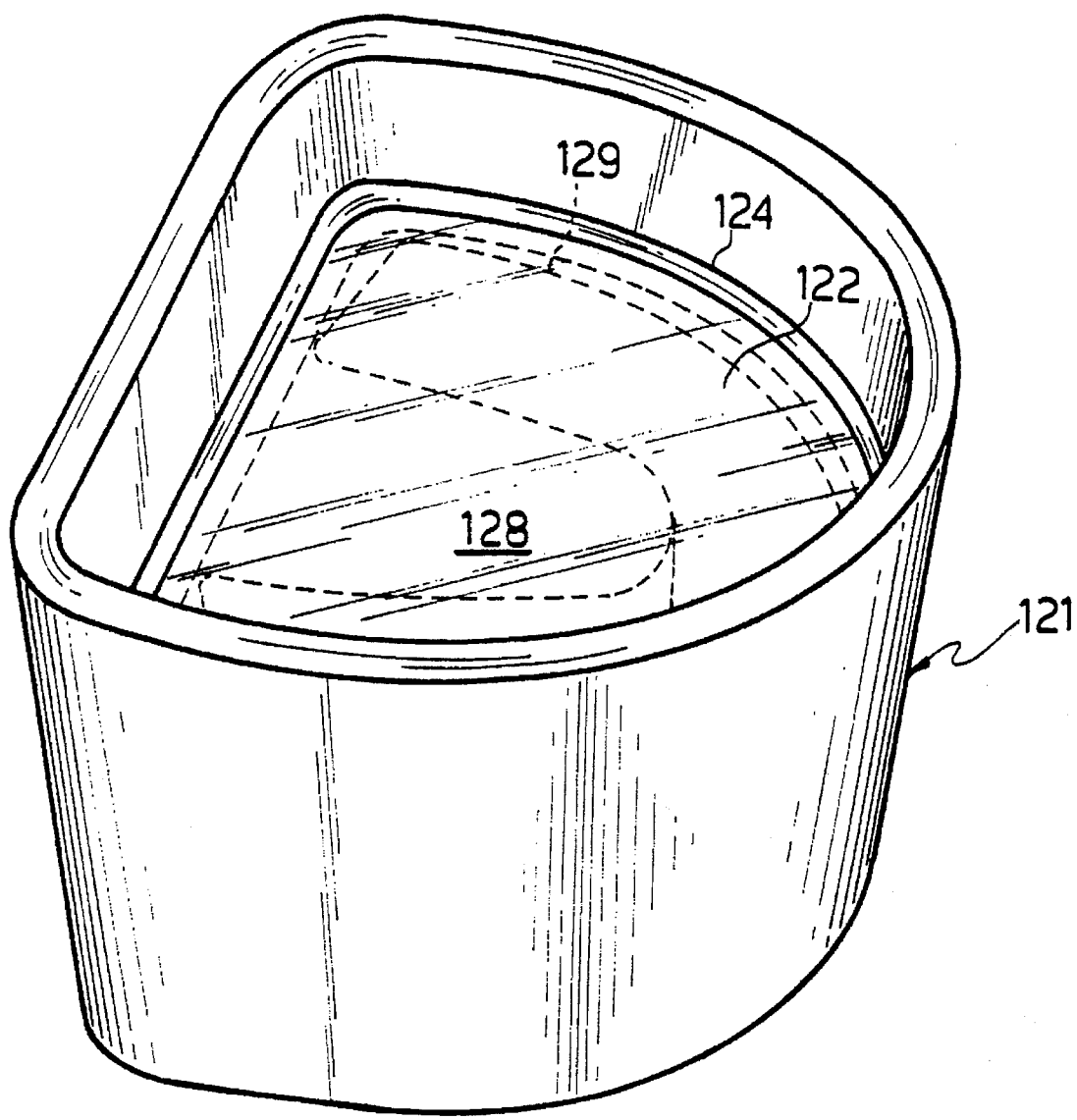
FIG. 22 is a perspective view of a second element of a second embodiment of the set for casting of gypsum models according to the invention.
Figure 26:
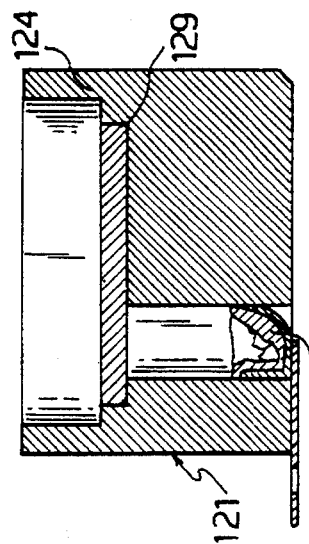
FIG. 26 is a section view along the line XXVI—XXVI of FIG. 25.

Said element 21 is realized with silicone material and provides an inner zone 22, coupable with the impression carrier 23 shown in FIG. 17, by which the patient impression has been taken in the usual manner, and a first step 24 connecting a containment superior zone 25 to impede the coming out of the cast gypsum.

The element 21 further provides a second step 29, for the insertion of a Plexiglas plate 30, the utilization of which will be described in greater detail in the following, upon which the metal pins 31 (FIGS. 20 and 21) are placed.

Figure 19:
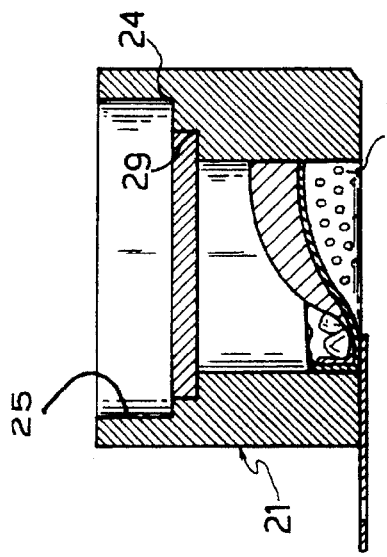
FIG. 19 is a section view along the line XIX—XIX of FIG. 18.
Figure 18:
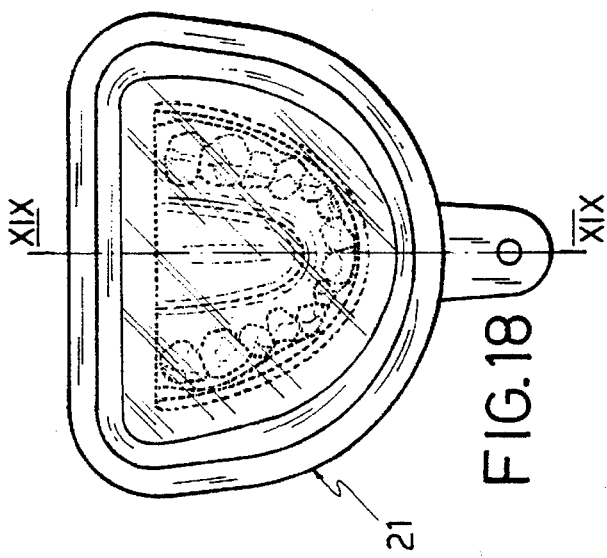
FIG. 18 is a plan view of the element of FIG. 15 and of the impression carrier of FIG. 17 coupled.

The impression carrier 23 and the element 21 couple each other as shown in FIGS. 18 and 19.

Figure 20:
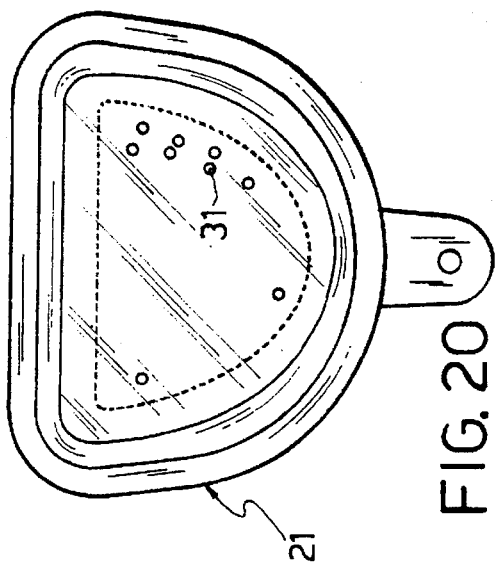
FIG. 20 is a plan view of the components of FIG. 18 after the casting of the gypsum with the perspex base and the pins inserted.
Figure 16:
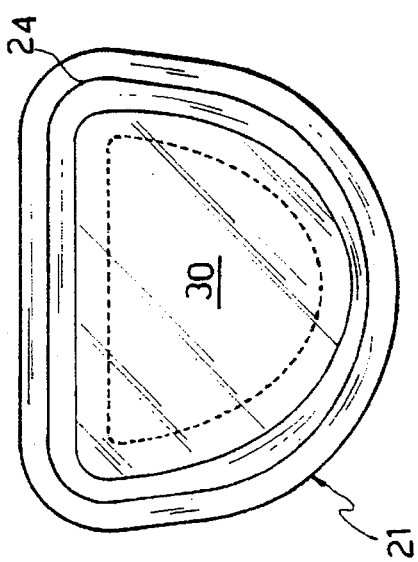
FIG. 16 is a plan view of the element of FIG. 15.

FIG. 20 shows the element 21 and the impression carrier 23 after the casting of the gypsum and after having placed above the same the Plexiglas plate 30 and the pins 31.

Figure 21:
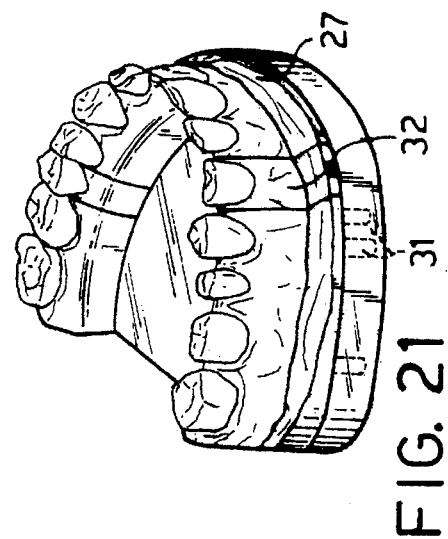
FIG. 21 is a perspective view of a model realized by the set according to the invention.

FIG. 21 shows the final result, with the obtained model 27.

In FIGS. 22 to 28 an element 121, and the relevant use, is shown, suitable for the lingual zone of the mouth.

Substantially, the functionality of the element 121, and its realization, are similar to those of the element 21 described above, so that the same elements and features are indicated by the same numeral reference, preceded by the number 1.

The difference that can be noted is the one relevant to the shaped projection 128 corresponding to the shaping of the impression carrier 123.

This second embodiment of the set according to the invention is particularly suitable for the utilization in working with the Zeiser system.

In this case the following procedure can be followed.

First, the exceeding impression material (alginate or silicone) coming out from the impression carrier 23 (123) is eliminated by a lancet or a cutter so as to obtain a perfect insertion and adhesion between the two parties (the impression and the element walls 21 (121)).

The element 21 (121) is brought with the impression carrier 23 (123) inserted on the device for piercing the gypsum, and the Plexiglas plate 30 (130) is restrained in the first step 29 (129).

It can be noted the grip of the plate 30 (130) within its housing, and the points where the holes for the insertion of the metal pins 31 (131) are marked.

Subsequently, the Plexiglas plate 30 (130) is disconnected and turned over in order to stress the point where the holes for the holding for the placement in the articulator.

On the device for piercing the gypsum holes are realized in correspondence of the marked points on both sides.

Now the metal pins 31 (131) are inserted in the realized holes.

Figure 27:
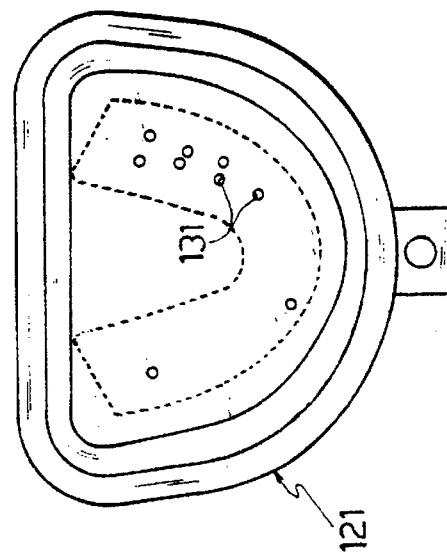
FIG. 27 is a plan view of the components of FIG. 25 after the casting of the gypsum.
Figure 23:
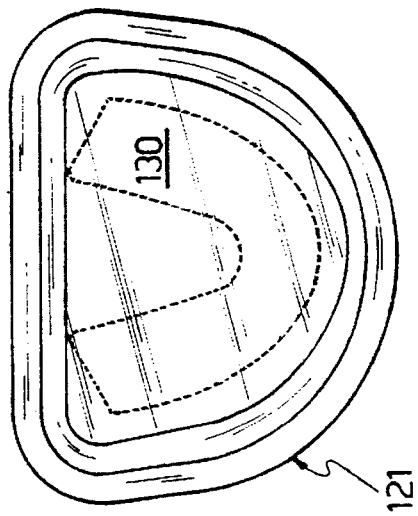
FIG. 23 is a plan view of the element of FIG. 22.
Figure 24:
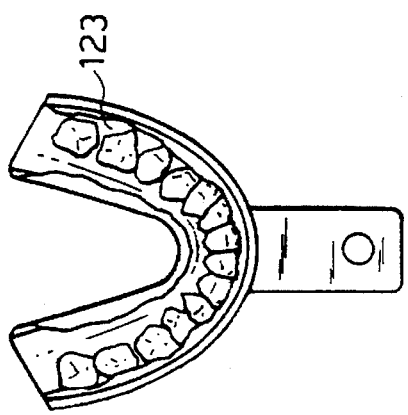
FIG. 24 is a plan view of an impression carrier usable with the element of FIG. 22.

Subsequently, the impression is cast employing a hard gypsum, said impression being filled in up to the base of the first step 29 (129) and then the Plexiglas plate 30 (130) is inserted in its seat with the pins 31 (131) buried within the gypsum (see FIGS. 20 and 27).

When the gypsum hardened, the model 27 (127) is removed along with the plate 30 (130) from the element 21 (121), it is disconnected from the Plexiglas plate 30 (130) and is refined by a gypsum tool, and then it is inserted again in the Plexiglas plate 30 (130).

Figure 28:
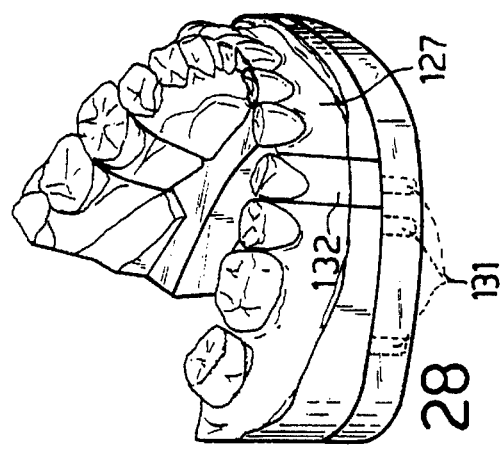
FIG. 28 is a perspective view of a model realized by the set according to the invention with the perspex base and the pins inserted.
Figure 25:
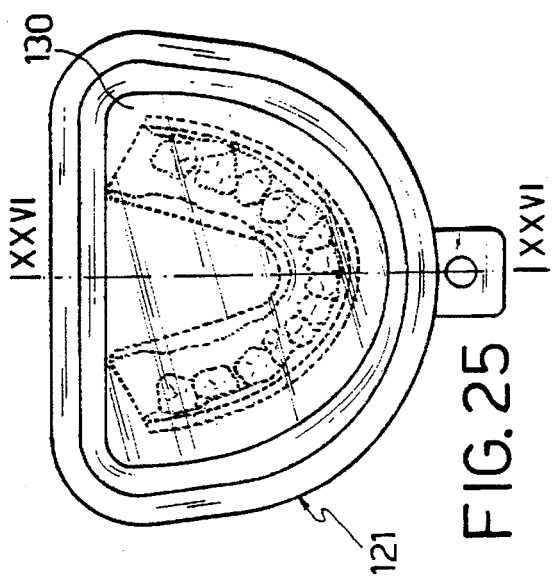
FIG. 25 is a plan view of the element of FIG. 22 and of the impression carrier of FIG. 24 coupled.

Now the gypsum model 27 (127) is inserted in the Plexiglas plate 30 (130) on the stub hacksaw and the teeth 32 (132) with the inserted pins are separated from the arcade (see FIGS. 21 and 28).

Finally, the gypsum stubs are discarded and refined, and then they are inserted on the plate 30 (130).

In this case too, on the known articulator, for example the Japanese one J. Morita or the Galletti articulator, it can be noted that the perfect refining of the model allows a precise restrain with articulator basis.

The present invention has been described for illustrative, but not limitative purposes, according to its preferred embodiments, but it is to be understood that modification and/or changes can be introduced by those skilled in the art without departing from the relevant scope as defined in the enclosed claims.

I claim:

1. A set of casting elements for the realization of gypsum models for dental prothesis, comprising a series of flexible rubber elements each element having an open top and an open bottom defined therein and being perimetrically closed and shaped in such a way to allow inner coupling of a corresponding impression carrier in said open bottom.

2. Set of casting elements for the realization of gypsum models for dental prosthesis according to claim 1, characterized in that said elements are made up of silicone material.

3. A casting method for the realization of gypsum models for dental prothesis employing the elements according to claim 1, comprising the steps of:

taking an impression with an impression carrier;

removing material exceeding said impression carrier;

introducing said impression carrier into a corresponding element;

closing slits using a suitable material;

casting gypsum; and disconnecting said impression.

4. A casting method for the realization of gypsum models for dental prothesis employing the elements according to claim 1, comprising the steps of:

taking an impression with an impression carrier;

removing material exceeding said impression carrier;

introducing said impression carrier into a corresponding element;

closing slits using a suitable material;

introducing a plurality of pins on teeth prepared in said impression;

covering an end of said pins with a wax ball;

casting gypsum up to an initial part of said pins;

after hardening, isolating said gypsum in correspondence of said pins, and completing a casting of said impression employing gypsum having a different color; and after said casting and hardening of said gypsum, separating teeth provided with said pins.

5. A casting method for the realization of gypsum models for dental prosthesis employing the elements according to claim 1, comprising the steps of:

taking an impression with an impression carrier;

removing material exceeding said impression carrier;

introducing said impression carrier into a corresponding element;

closing slits using a suitable material;

bringing said element with said impression carrier introduced in said element for piercing gypsum, introducing a plate and marking pin positioning points;

releasing and turning over said plate and realizing holes for a plurality of pins;

introducing said pins in their position;

casting a hard gypsum and placing again said plate;

after hardening, removing the model with said plate and refining the same;

separating teeth provided with said pins.

6. A set of casting elements for the realization of gypsum models for dental prothesis, comprising:

a series of rubber elements having an open top and an open bottom defined therein, each of said elements being perimetrically closed and shaped to allow inner coupling of a corresponding impression carrier in said open bottom; and a first step provided on an interior surface of each of said elements, said first step being positioned above a zone having dimensions corresponding to the dimensions of a gypsum model to be formed, said first step preventing lateral leakage of cast gypsum from said zone.

7. A set of casting elements for the realization of gypsum models for dental prosthesis according to claim 6 further comprising a second step provided for the introduction of a plate for positioning a plurality of pins, said second step being provided together or independently from said first step.

8. A set of casting elements for the realization of gypsum models for dental prosthesis according to claim 7, wherein each of said elements is provided with a central projection thereon corresponding to a shape of a jaw.

9. A casting method for the realization of gypsum models for dental prosthesis employing the elements according to claim 7, comprising the steps of:

taking an impression with an impression carrier;

removing material exceeding said impression carrier;

introducing said impression carrier into a corresponding element;

closing slits using a suitable material;

casting gypsum; and disconnecting said impression.

10. A set of casting elements for the realization of gypsum models for dental prosthesis according to claim 6, wherein each of said elements further include therein a central projection corresponding to a shape of a jaw.

11. A casting method for the realization of gypsum models for dental prosthesis employing the elements according to claim 10, comprising the steps of:

taking an impression with an impression carrier;

removing material exceeding said impression carrier;

introducing said impression carrier into a corresponding element;

closing slits using a suitable material;

casting gypsum; and disconnecting said impression.

12. A set of casting elements for the realization of gypsum models for dental prosthesis according to claim 6, further comprising a second step provided for introduction of a plate for positioning at least one pin, said second step being provided together or independently from said first step.

13. A set of casting elements for the realization of gypsum models for dental prosthesis according to claim 6, wherein each of said elements is provided with a central projection thereon corresponding to a shape of a jaw.

14. A casting method for the realization of gypsum models for dental prosthesis employing the elements according to claim 6, comprising the steps of:

taking an impression with an impression carrier;

removing material exceeding said impression carrier;

introducing said impression carrier into a corresponding element;

closing slits using a suitable material;

casting gypsum; and disconnecting said impression.

15. A set of casting elements for the realization of gypsum models for dental prosthesis, comprising a series of rubber elements made of silicone material, each element having an open top and an open bottom defined therein and being perimetrically closed and shaped to allow inner coupling of a corresponding impression carrier in said open bottom; and a first step provided on an interior surface of each of said elements above a zone having dimensions corresponding to dimensions of a gypsum model to be formed, said first step preventing a lateral leakage of cast gypsum from said zone.

16. A set of casting elements for the realization of gypsum models for dental prosthesis, according to claim 15, further comprising:

a second step, provided for introduction of a plate for positioning at least one pin, said second step being provided together or independently from said first step.

17. A set of casting elements for the realization of gypsum models for dental prosthesis, according to claim 15, wherein each of said elements is provided with a central projection thereon corresponding to a shape of a jaw.

18. A casting method for the realization of gypsum models for dental prosthesis employing a series of flexible rubber elements made of silicone material, each element having an open top and an open bottom defined therein and being perimetrically closed and shaped in such a way to allow inner coupling of a corresponding impression carrier in said open bottom, comprising the steps of:

taking an impression with an impression carrier;

removing material exceeding said impression carrier;

introducing said impression carrier into a corresponding element;

closing slits using a suitable material;

casting gypsum; and disconnecting said impression.

19. A casting method for the realization of gypsum models for dental prosthesis employing a series of flexible rubber elements made of silicone material, each element having an open top and an open bottom defined therein and being perimetrically closed and shaped in such a way to allow inner coupling of a corresponding impression carrier in said open bottom, comprising the steps of:

taking an impression with an impression carrier;

removing material exceeding said impression carrier;

introducing said impression carrier into a corresponding element;

closing slits using a suitable material;

introducing pins on teeth prepared in said impression;

covering an end of said pins with a wax ball;

casting gypsum up to an initial part of said pins;

after hardening, isolating said gypsum in correspondence of said pins, and completing casting of said impression employing gypsum having a different color;

after casting and hardening of said gypsum, separating teeth provided with said pins.

20. A casting element for the realization of gypsum models for dental prothesis, comprising:

a rubber element having an open top and an open bottom defined therein and being perimetrically closed and shaped in such a way to allow inner coupling of a corresponding impression carrier in said open bottom.

21. A casting element for the realization of gypsum models for dental prothesis as defined in claim 20, further comprising:

a step provided on an interior of said rubber element, said step being positioned above a zone having dimensions corresponding to a model to be formed.

* * * * *